(12) United States Patent
Hasegawa (10) Patent No.: US 12,306,394 B2
(45) Date of Patent: May 20, 2025

(54) OBJECTIVE OPTICAL SYSTEM, METHOD OF MANUFACTURING OBJECTIVE OPTICAL SYSTEM IMAGE PICKUP APPARATUS, AND ENDOSCOPE

(71) Applicant: OLYMPUS CORPORATION, Hachioji (JP)

(72) Inventor: Naoki Hasegawa, Chofu (JP)

(73) Assignee: OLYMPUS CORPORATION, Tokyo (JP)

( * ) Notice: Subject to any disclaimer, the term of this patent is extended or adjusted under 35 U.S.C. 154(b) by 578 days.

(21) Appl. No.: 17/704,067

(22) Filed: Mar. 25, 2022

(65) Prior Publication Data

US 2022/0214534 A1 Jul. 7, 2022

Related U.S. Application Data

(63) Continuation of application No. PCT/JP2019/044107, filed on Nov. 11, 2019.

(51) Int. Cl.
*A61B 1/00* (2006.01)
*G02B 13/04* (2006.01)
*G02B 23/24* (2006.01)
*G02B 23/26* (2006.01)

(52) U.S. Cl.
CPC ........ *G02B 23/243* (2013.01); *A61B 1/00096* (2013.01); *G02B 13/04* (2013.01); *G02B 23/26* (2013.01)

(58) Field of Classification Search
CPC ...... G02B 23/243; G02B 13/04; G02B 23/26; A61B 1/00096
See application file for complete search history.

(56) References Cited

U.S. PATENT DOCUMENTS

| 6,905,462 B1 * | 6/2005 | Homma ............... G02B 23/243 |
| | | 348/340 |
| 8,331,045 B2 | 12/2012 | Suzuki et al. |
| 8,715,170 B2 | 5/2014 | Kanazawa et al. |

(Continued)

FOREIGN PATENT DOCUMENTS

| JP | H10123411 A | 5/1998 |
| JP | 2002365535 A | 12/2002 |

(Continued)

OTHER PUBLICATIONS

International Search Report (ISR) (and English language translation thereof) dated Dec. 10, 2019, issued in International Application No. PCT/JP2019/044107.

(Continued)

*Primary Examiner* — Mustak Choudhury
(74) *Attorney, Agent, or Firm* — Holtz, Holtz & Volek PC (57) ABSTRACT

The objective optical system includes a flat plate disposed closest to an object side and a plano-concave negative lens having a flat surface facing the object side. The flat plate is a transparent material harder than the plano-concave lens. The flat plate and the plano-concave lens having an equal diameter are bonded. The following Conditional Expressions (1) and (7) are satisfied:

$10 \leq \varphi 1/t1 \leq 70$ (1)

$7 \leq \varphi 1/(t1+t2) \leq 9.71$ (7)

where
$\varphi 1$ is an outer diameter of the flat plate,
t1 is a thickness of the flat plate, and
t2 is a thickness of the plano-concave negative lens along an optical axis.

16 Claims, 8 Drawing Sheets

(56) References Cited

U.S. PATENT DOCUMENTS

| | | | |
|---|---|---|---|
| 8,976,468 | B2 | 3/2015 | Kanazawa et al. |
| 10,330,898 | B2* | 6/2019 | Sugiyama .......... G02B 13/0045 |
| 10,680,134 | B2 | 6/2020 | Kashima et al. |
| 10,950,751 | B2 | 3/2021 | Kashima et al. |
| 11,089,948 | B2 | 8/2021 | Khettal et al. |
| 2011/0013294 | A1 | 1/2011 | Suzuki et al. |
| 2014/0018628 | A1 | 1/2014 | Kanazawa et al. |
| 2014/0198398 | A1* | 7/2014 | Kanazawa .......... G02B 23/243 359/783 |
| 2018/0248075 | A1* | 8/2018 | Kashima ................. H01L 33/20 |
| 2018/0360298 | A1 | 12/2018 | Khettal et al. |
| 2020/0313041 | A1 | 10/2020 | Kashima et al. |

FOREIGN PATENT DOCUMENTS

| | | | |
|---|---|---|---|
| JP | 2004107602 | A | 4/2004 |
| JP | 2011022444 | A | 2/2011 |
| JP | 5274728 | B2 | 5/2013 |
| JP | 2018182172 | A | 11/2018 |
| JP | 2019032510 | A | 2/2019 |
| WO | 0118585 | A1 | 3/2001 |
| WO | 2017038961 | A1 | 3/2017 |
| WO | 2019180979 | A1 | 9/2019 |

OTHER PUBLICATIONS

Written Opinion dated Dec. 10, 2019, issued in International Application No. PCT/JP2019/044107.

International Preliminary Report on Patentability (IPRP) (and English language translation thereof) dated May 27, 2022, issued in counterpart International Application No. PCT/JP2019/044107.

Japanese Office Action dated Jan. 27, 2023 (and English translation thereof) issued in counterpart Japanese Application No. 2021-555629.

* cited by examiner

OBJECTIVE OPTICAL SYSTEM, METHOD OF MANUFACTURING OBJECTIVE OPTICAL SYSTEM IMAGE PICKUP APPARATUS, AND ENDOSCOPE

CROSS REFERENCES

The present application is a continuation application of PCT/JP2019/044107 filed on Nov. 11, 2019; the entire contents of which are incorporated herein by reference.

BACKGROUND OF INVENTION

Technical Field

The disclosure relates to an objective optical system, an image pickup apparatus, an endoscope, and a method of manufacturing an objective optical system.

Description of the Related Art

In the medical field, endoscopes are used to observe a region deep inside the body cavity by inserting an elongated insertion part into the body cavity and to perform medical treatment, if necessary, by using a treatment tool. Objective optical systems for endoscopes are disclosed, for example, in Japanese Unexamined Patent Application Publication No. 2019-32510, Japanese Unexamined Patent Application Publication No. 2002-365535, and Japanese Patent No. 5274728.

SUMMARY

An objective optical system according to at least some embodiments of the present disclosure includes a flat plate disposed closest to an object side and a plano-concave negative lens having a flat surface facing the object side, in which
the flat plate is a transparent material harder than the plano-concave negative lens,
the flat plate and the plano-concave negative lens are bonded, and
the following Conditional Expressions (1) and (7) are satisfied:

$$10 \leq \varphi 1/t1 \leq 70 \quad (1)$$

$$7 \leq \varphi 1/(t1+t2) \leq 9.71 \quad (7)$$

where
$\varphi 1$ is an outer diameter of the flat plate,
$t1$ is a thickness of the flat plate, and
$t2$ is a thickness of the plano-concave negative lens along an optical axis.

In another aspect, a method of manufacturing an objective optical system according to at least some embodiments of the present disclosure includes the steps of:
providing a first substrate made of a transparent material;
providing a second substrate made of an optical glass to form a plano-concave negative lens;
activating and bonding the first substrate and the second substrate;
making the activated and bonded first substrate and second substrate into thin pieces, the first substrate and the second substrate each having dimensions corresponding to a plurality of the plano-concave negative lenses; and
performing lens processing on the second substrate after the step of making thin pieces, in which
the first substrate is a material harder than the second substrate, and
the following Conditional Expressions (1) and (7) are satisfied:

$$10 \leq \varphi 1/t1 \leq 70 \quad (1)$$

$$7 \leq \varphi 1/(t1+t2) \leq 9.71 \quad (7)$$

where
$\varphi 1$ is an outer diameter of the first substrate,
$t1$ is a thickness of the first substrate, and
$t2$ is a thickness of the second substrate along an optical axis.

In another aspect, an image pickup apparatus according to at least some embodiments of the present disclosure includes:
an objective optical system; and
an imager, in which
the objective optical system is the objective optical system described above.

In another aspect, an endoscope according to at least some embodiments of the present disclosure includes:
an objective optical system; and
an imager, in which
the objective optical system is the objective optical system described above.

DETAILED DESCRIPTION

Prior to a description of examples, operation effects of embodiments according to some aspects of the present disclosure will be described. In a specific description of operation effects of the embodiments, specific examples will be described. However, the examples described later as well as the illustrative embodiments are only some of the embodiments encompassed by the present disclosure, and the embodiments include numerous variations. Therefore, the present disclosure is not intended to be limited to the illustrative embodiments.

First Embodiment

Figure 1A:
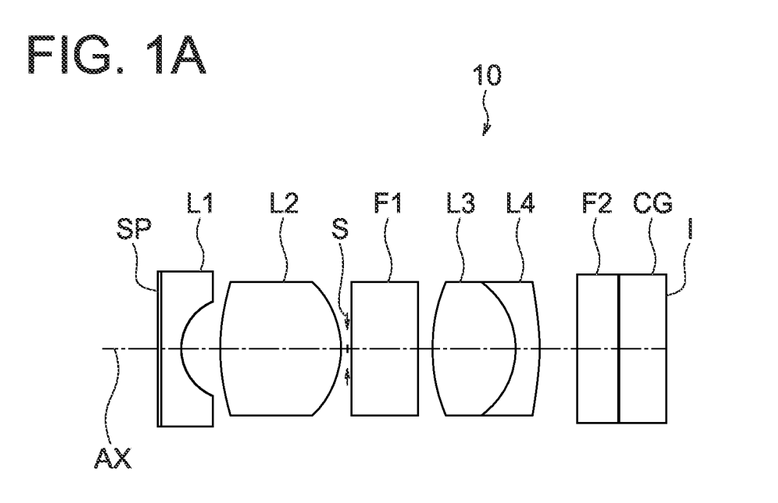
FIG. 1A is a lens cross-sectional view of an objective optical system according to a first embodiment.

FIG. 1A is a lens cross-sectional view of an objective optical system 10 according to a first embodiment. The objective optical system 10 includes, in order from an object side to an image side, a flat plate SP, a plano-concave negative lens L1 having a flat surface facing the object side, a biconvex positive lens L2, an aperture stop S, a parallel flat plate F1, a biconvex positive lens L3, a negative meniscus lens L4 having a convex surface facing the image side, a parallel flat plate F2, and a cover glass CG.

The objective optical system 10 includes the flat plate SP disposed closest to the object side and the plano-concave negative lens L1 having a flat surface facing the object side. The flat plate SP is a transparent material harder than the plano-concave negative lens L1. The flat plate SP and the plano-concave negative lens L1 are bonded. The following Conditional Expressions (1) and (7) are satisfied:

$$10 \leq \varphi1/t1 \leq 70 \tag{1}$$

$$7 \leq \varphi1/(t1+t2) \leq 9.71 \tag{7}$$

where
φ1 is the outer diameter of the flat plate SP,
t1 is the thickness of the flat plate SP, and
t2 is a thickness of the plano-concave negative lens along an optical axis.

Figure 1B:
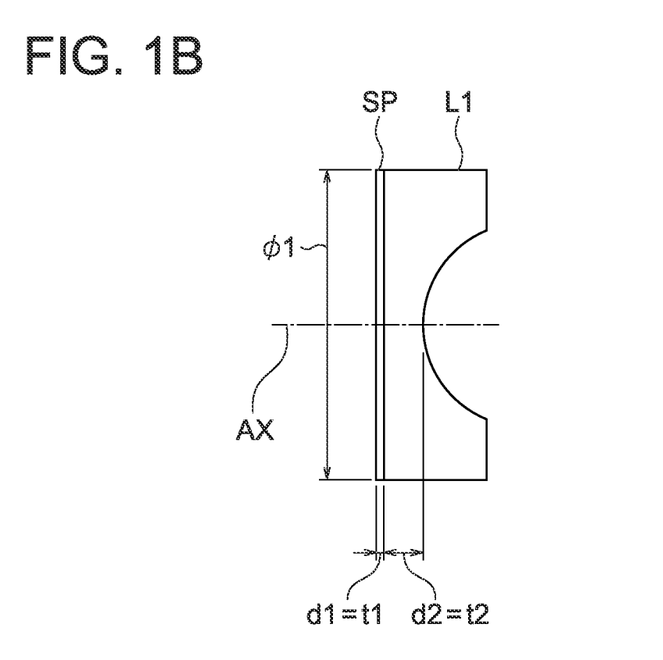
FIG. 1B is a lens cross-sectional view of a flat plate and a plano-concave negative lens at a distal end.

FIG. 1B is a cross-sectional view of a lens configuration at a distal end closest to the object side in the objective optical system 10. The flat plate SP is, for example, sapphire glass or transparent ceramics.

Conditional Expression (1) defines an appropriate ratio between the outer diameter φ1 of the flat plate SP formed of sapphire glass and the thickness t1 of the flat plate SP.

By satisfying Conditional Expression (1), it is possible to release stress, because the flat plate SP is deformed when bending stress is produced in the plano-concave negative lens L1.

When a value falls below the lower limit value of Conditional Expression (1), the thickness t1 of the flat plate SP increases. As the thickness t1 of the flat plate SP increases, the flat plate SP is less deformable. If the flat plate SP is bonded to the plano-concave negative lens L1 in this state, stress is likely to be concentrated on the bonding surfaces. Furthermore, as the thickness t1 of the flat plate SP increases, light rays are vignetted. To ensure a wide angle of view so that light rays are not vignetted, the size of the objective optical system is increased.

When a value exceeds the upper limit value of Conditional Expression (1), the thickness t1 of the flat plate SP decreases. As a result, the flat plate SP is easily deformed and lacks mechanical strength. If the mechanical strength of the flat plate SP is lacking, the flat plate SP may be cracked or broken.

When a value falls below the lower limit value of Conditional Expression (7), the sum of the thickness along the optical axis becomes large in relation to the outer diameter. Vignetting of the light beam is occurred. In order to secure a wide viewing angle so that the light beam is not vignetted, the objective optical system becomes larger.

When a value exceeds the upper limit value of Conditional Expression (7) is exceeded, the sum of the thickness along the optical axis becomes small in relation to the outer diameter. Lenses are difficult to make because they are prone to cracking when making spherical segment.

Furthermore, it is preferable that Conditional Expression (1') is satisfied instead of Conditional Expression (1).

$$12 \leq \varphi1/t1 \leq 50 \tag{1'}$$

Furthermore, it is further preferable that Conditional Expression (1") is satisfied instead of Conditional Expression (1).

$$14 \leq \varphi1/t1 \leq 34 \tag{1"}$$

Furthermore, according to a preferred mode of the present embodiment, it is preferable that the flat plate SP and the plano-concave negative lens L1 are bonded by activated bonding.

"Activated bonding" means that material surfaces of substrates (the surfaces to be bonded) are activated and bonded directly by intermolecular forces. In activated bonding, no organic adhesive (polymer adhesive, hereinafter referred to as "adhesive" if necessary) is interposed between the substrates. It is therefore possible to make the bonded interface more reliable by "activated bonding" than by "bonding" with adhesive.

In the present embodiment, it is preferable to use, for example, surface activated bonding and plasma activated bonding, among activated bonding processes.

The detail of "activated bonding" will be described in a second embodiment (a method of manufacturing an objective optical system). A configuration including a lens and a filter bonded by adhesive is referred to as a cemented lens as conventionally called. In the present disclosure, "activated bonded lens" is a configuration different from "cemented lens using an organic adhesive".

According to a preferred mode of the present embodiment, it is preferable that the following Conditional Expression (2) is satisfied:

$$0.1 \leq t1/t2 \leq 1.4 \tag{2}$$

where t1 is the thickness of the flat plate SP, and t2 is the thickness of the plano-concave negative lens L1 along the optical axis AX.

Conditional Expression (2) defines an appropriate ratio between the thickness t1 of the flat plate SP and the thickness t2 of the plano-concave negative lens L1 along the optical axis AX.

When a value falls below the lower limit value of Conditional Expression (2), the thickness of the flat plate SP decreases. As the thickness of the flat plate SP decreases, the flat plate SP is more easily deformed. Thus, it is possible to release the stress in activated bonding. However, the mechanical strength of the surface of the flat plate SP is insufficient.

When a value exceeds the upper limit value of Conditional Expression (2), the thickness t1 of the flat plate SP increases and the flat plate SP is less deformable. Therefore, the plano-concave negative lens L1 is also not deformable. Thus, material failure such as separation of the activated bonding surfaces and breaking of the plano-concave negative lens L1 is likely to occur.

Furthermore, it is preferable that Conditional Expression (2') is satisfied instead of Conditional Expression (2).

$$0.2 \leq t1/t2 \leq 1.2 \tag{2'}$$

Furthermore, it is further preferable that Conditional Expression (2") is satisfied instead of Conditional Expression (2).

$$0.4 \leq t1/t2 \leq 1.0 \tag{2"}$$

According to a preferred mode of the present embodiment, it is preferable that the following Conditional Expression (3) is satisfied:

$$0.4 \leq (t1/t2) \times (e1/e2) \leq 5 \tag{3}$$

where t1 is the thickness of the flat plate SP, t2 is the thickness of the plano-concave negative lens L1 along the optical axis AX, e1 is the elastic modulus of the flat plate SP, and e2 is the elastic modulus of the plano-concave negative lens L1.

Conditional Expression (3) defines an appropriate division ratio between the thicknesses t1 and t2 along the optical axis AX. The thickness t2 of the plano-concave negative lens L1 is uneven, where the center is thin and the periphery is thick. Thus, the plano-concave negative lens L1 is likely to suffer bending stress when it is processed or assembled.

Sapphire glass has a higher elastic modulus and is harder than optical glass. The flat plate SP of sapphire glass therefore constrains the deformation of the plano-concave negative lens L1.

Furthermore, the flat plate SP of sapphire and the plano-concave negative lens L1 are activated and bonded. The stress is then concentrated on the bonded interface. It is therefore preferable that Conditional Expression (3) is satisfied in order to perform activated bonding more favorably by reducing the stress.

When a value falls below the lower limit value of Conditional Expression (3), the thickness t1 of the flat plate SP of sapphire glass decreases. As the thickness t1 of the flat plate SP decreases, the flat plate SP is more easily deformed. It is possible to release the stress in activated bonding because the flat plate SP is deformable. However, the mechanical strength of the surface of the flat plate SP is insufficient.

When a value exceeds the upper limit value of Conditional Expression (3), the thickness t1 of the flat plate SP increases and the flat plate SP is less deformable. Therefore, the plano-concave negative lens L1 is also not deformable. Thus, material failure such as separation of the activated bonding surfaces and breaking of the plano-concave negative lens L1 is likely to occur.

According to a preferred mode of the present embodiment, it is preferable that the following Conditional Expression (4) is satisfied:

$$|v1-v2|/\text{Max}(v1,v2) \leq 0.2 \quad (4)$$

where v1 is the coefficient of linear expansion of the flat plate SP, v2 is the coefficient of linear expansion of the plano-concave negative lens L1, and Max(v1,v2) is the larger value of v1 and v2.

Conditional Expression (4) defines an appropriate combination of the coefficient of linear expansion v1 of the flat plate SP and the coefficient of linear expansion v2 of the plano-concave negative lens L1. By satisfying Conditional Expression (4), it is possible to avoid thermal stress in processing, assembly, and use environment when the flat plate SP and the plano-concave negative lens L1 are activated and bonded.

According to a preferred mode of the present embodiment, it is preferable that the following Conditional Expression (5) is satisfied:

$$120° \leq \omega \quad (5)$$

where ω is the angle of view of the objective optical system 10.

By satisfying Conditional Expression (5), it is possible to obtain the objective optical system 10 having a wide angle of view of 120° or more.

According to a preferred mode of the present embodiment, it is preferable that the following Conditional Expression (6) is satisfied:

$$1.8 \leq n2 \leq 2.2 \quad (6)$$

where n2 is the refractive index of the plano-concave negative lens L1 for d-line.

When a value falls below the lower limit value of Conditional Expression (6), it is difficult to reduce the size of the lens in the radial direction at the distal end at a time of a wide angle of 120° or more.

When a value exceeds the upper limit value of Conditional Expression (6), the reflection at the bonded interface between the flat plate SP and the plano-concave negative lens L1 increases. Accordingly, ghosts and/or flare become noticeable to impair the image quality. Furthermore, choosing a glass material becomes difficult.

Second Embodiment

The present embodiment relates to a method of manufacturing the objective optical system described above. It is necessary to satisfy both of design requirements such as size reduction in the radial direction at a time of a wide angle of the objective optical system and improvement in mechanical strength of the lens surface. To do so, in the present embodiment, the flat plate SP of a thin transparent material and the plano-concave negative lens L1 formed of a high refractive index material are integrated by activated bonding.

The flat plate SP and the plano-concave negative lens L1 are integrated by activated bonding. It is therefore possible to minimize the thicknesses of the flat plate SP and the plano-concave negative lens L1. As a result, it is possible that the objective optical system manufactured by the present embodiment has a wide angle of view of 120° or more and has a lens reduced in size in the radial direction.

Figure 2A:
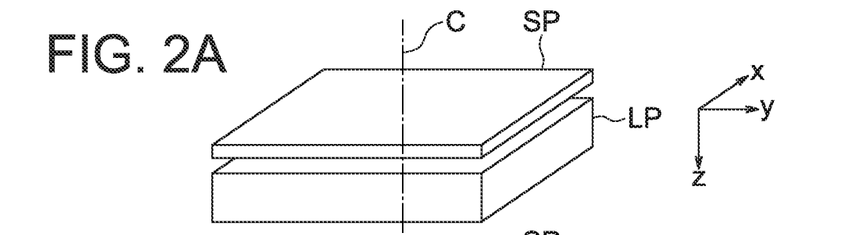
FIG. 2A, FIG. 2B, FIG. 2C, FIG. 2D, FIG. 2E, and FIG. 2F are diagrams illustrating a method of manufacturing an objective optical system according to a second embodiment.

FIG. 2A, FIG. 2B, FIG. 2C, FIG. 2D, FIG. 2E, and FIG. 2F are diagrams illustrating the method of manufacturing an objective optical system according to the second embodiment. FIG. 3 is a flowchart illustrating the method of manufacturing an objective optical system according to the second embodiment.

The method of manufacturing an objective optical system of the present embodiment includes the steps of:

providing a first substrate SP made of a transparent material (step S101 in FIG. 3);

providing a second substrate LP made of an optical glass to form the plano-concave negative lens L1 (step S102 in FIG. 3);

activating and bonding the first substrate SP and the second substrate LP (step S103 in FIG. 3);

making the activated and bonded first substrate SP and second substrate LP into thin pieces, the first substrate SP and the second substrate LP each having dimensions corresponding to a plurality of the plano-concave negative lenses L1 (step S104 in FIG. 3); and performing lens processing on the second substrate LP after the step of making thin pieces (step S105 in FIG. 3), in which the first substrate SP is a material harder than the second substrate LP, and the following Conditional Expressions (1) and (7) are satisfied:

$$10 \leq \varphi1/t1 \leq 70 \quad (1)$$

$$7 \leq \varphi1/(t1+t2) \leq 9.71 \quad (7)$$

where

φ1 is an outer diameter of the first substrate, t1 is a thickness of the first substrate, and t2 is a thickness of the second substrate along an optical axis.

The first substrate SP is, for example, sapphire glass. FIG. 2A illustrates the first substrate SP of sapphire glass and the second substrate LP made of an optical glass to form the plano-concave negative lens L1. A C-plane product (a plane perpendicular to the C-axis that is a crystal axis) is used as the first substrate SP of sapphire glass. A light ray travels through the inside of the sapphire glass with the same refractive index along the C-axis of the sapphire glass (indicated by C in 2A).

Furthermore, according to a preferred mode of the present embodiment, it is preferable that the first substrate SP is sapphire glass.

The plane perpendicular to the C-axis of monocrystalline sapphire glass in the first substrate SP is activated and bonded to the second substrate LP.

A-plane products of sapphire glass are also available. The reason why the C-plane is used in the present embodiment instead of the A-plane of sapphire glass will be described below.

In an objective optical system having a wide angle of view of 120° or more, it is preferable to prevent one-sided blur due to decentration of the plano-concave negative lens L1 having a high refractive power. To do so, it is necessary to fit the plano-concave negative lens L1 in a holding frame with high accuracy. It is therefore necessary to finish the outer diameter of the plano-concave negative lens L1 with high accuracy.

A-plane products of sapphire glass have uneven hardness at the crystal periphery. Thus, the outer diameter fails to be a perfect circle in the centering process of sapphire glass, and there is a limit to high accuracy.

Furthermore, the use of A-plane products of sapphire glass may cause the following inconvenience.
  (1) A-plane products tend to have burrs (unnecessary protrusions produced in the processed surface) in a certain direction in centering.
  (2) A-plane products exhibit double refraction asymmetric to the optical axis. Therefore, in a wide field of view of the objective optical system, the peripheral image quality varies with places such as upper, lower, right, and left sides of the field of view.

Therefore, C-plane products of sapphire glass are used as in the present embodiment, whereby the double refraction becomes symmetric to the optical axis AX and the peripheral image quality becomes even. The hardness in the circumferential direction also becomes constant, so that the outer diameter can be processed accurately.

Figure 2B:
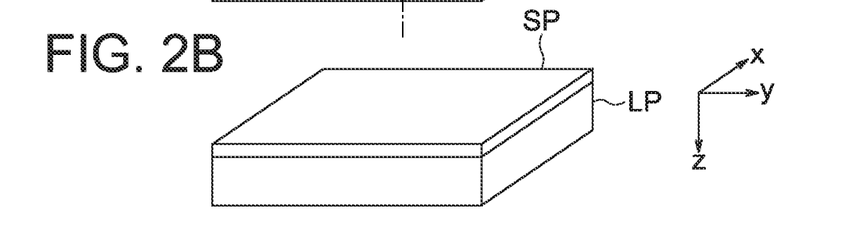
Figure 3:
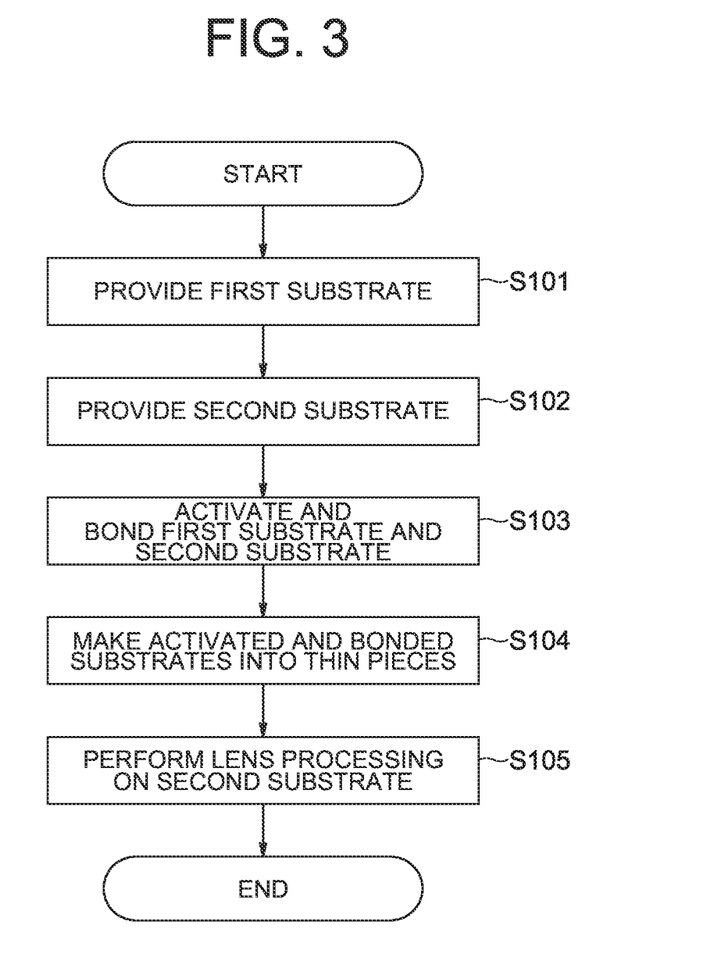
FIG. 3 is a flowchart illustrating the method of manufacturing an objective optical system according to the second embodiment.

FIG. 2B illustrates a configuration in which the first substrate SP of sapphire glass and the second substrate LP made of an optical glass to form the plano-concave negative lens L1 are activated and bonded.

The procedure for activating and bonding the first substrate SP and the second substrate LP will be described below. First, the first substrate SP having a size larger than the diameter of the plano-concave negative lens L1 at the distal end and the second substrate LP having a size larger than the diameter of the plano-concave negative lens L1 at the distal end are stably bonded by activated bonding.

The plano-concave negative lens L1 at the distal end of the objective optical system is exposed to the surrounding environment and chemicals. Thus, higher resistance is required. Therefore, a reliable bonding process is needed. Furthermore, the dimensions of the first substrate SP and the second substrate LP are the sizes in inches. Since the substrates thus sized in inches are bonded, bonding technology in semiconductor manufacturing, specifically the activated bonding technology described in the first embodiment is used in the present embodiment.

According to a preferred mode of the present embodiment, it is preferable that the step of activating and bonding includes a surface activated bonding step or a plasma activated bonding step.

In order to increase the adhesion between the first substrate SP of sapphire glass and the second substrate LP of optical glass, it is preferable that the surfaces of the first substrate SP and the second substrate LP are finished into smooth and flat surfaces by chemical mechanical polishing (CMP).

Examples of numerical values in CMP are listed below.
Surface roughness: Ra (arithmetic mean height)<1 nm
Maximum height: Rz<10 nm
Flatness<1 μm Here, the first substrate SP of sapphire glass, which is deformable and adherent, does not require the flatness described above.

In surface activated bonding, energetic particles such as ion beams are used to activate and bond the surface of the first substrate SP and the surface of the second substrate LP. Surface activated bonding is performed in an ultrahigh vacuum ($10^{-6}$ Pa). Furthermore, in surface activated bonding, unheated bonding at room temperature is possible.

In plasma activated bonding, bonding in atmospheric pressure is possible. The surfaces to be activated and bonded are exposed to plasma in advance for lowering the temperature of bonding. In the case of plasma activated bonding, it is preferable that the bonding is followed by low-temperature annealing at approximately 150° for stronger bonding.

Furthermore, it is also possible to use atomic diffusion bonding (ADB) to activate and bond substrates made of low activity materials. In atomic diffusion bonding, high activity metal thin films (Ti, Al, etc.) or Si thin films are formed on the surfaces, and thereafter diffusion bonding is performed in a vacuum.

Figure 2C:
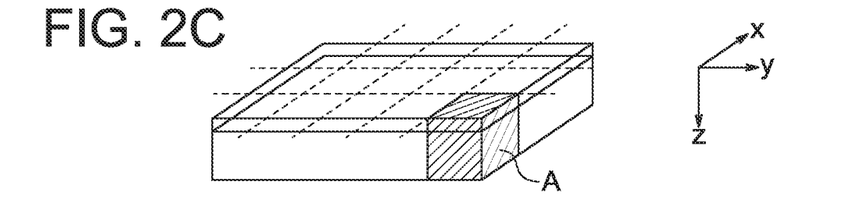

FIG. 2C illustrates a configuration in which the activated and bonded first substrate SP and second substrate LP are made into thin pieces. The first substrate SP and the second substrate LP have dimensions corresponding to a plurality of plano-concave negative lenses L1. Then, the activated and bonded first substrate SP and second substrate LP are made into thin pieces.

In making thin pieces, the activated and bonded first substrate SP and second substrate LP are processed into individual lenses A that are thin pieces as indicated by dotted lines in FIG. 2C, for example, by dicing. The activated and bonded substrates may be made into thin pieces in a rectangular shape or a circular shape (cylindrical shape), for example, by honing or laser processing, instead of dicing.

Figure 2D:
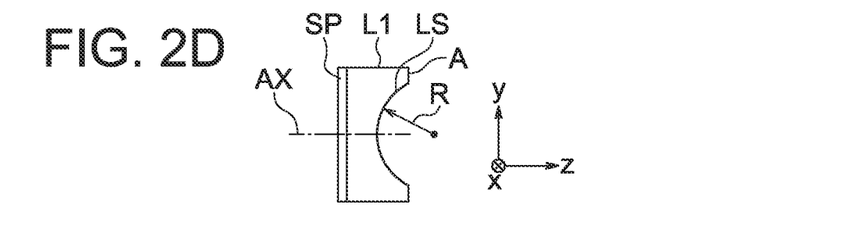
Figure 2E:
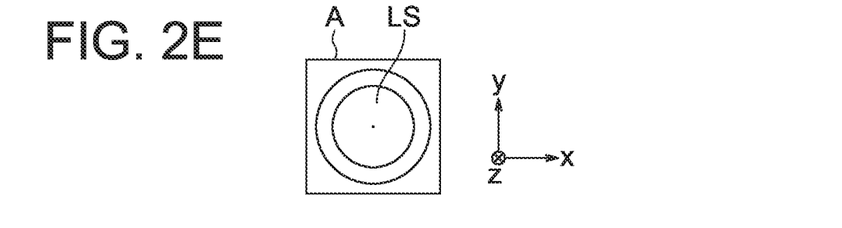
Figure 2F:
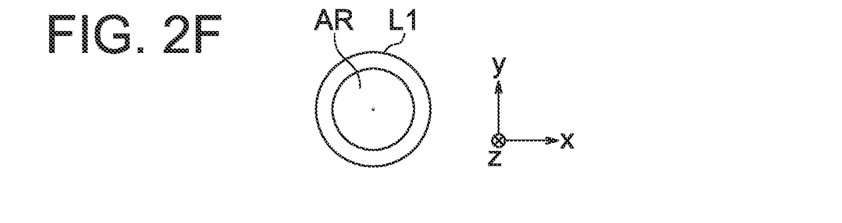

In FIG. 2D, each of the lenses A is processed by a not-illustrated cutter to make a spherical segment having a radius R, resulting in a concave surface LS. Furthermore, as illustrated in FIG. 2E, centering and chamfering are performed on the lens A to finish the shape. Finally, as illustrated in FIG. 2F, an anti-reflection coating AR is applied to complete the plano-concave negative lens L1.

Here, a conventional method may be contemplated, which performs bonding after processing into small and thin parts in advance. In the conventional method, two parts with a minimum thickness along the optical axis AX are bonded. Thus, the thickness of the bonded part along the optical axis AX is twice the thickness before bonding. Furthermore, the thickness accuracy of the bonded part along the optical axis is the sum of the accuracy of the two parts. Therefore, the thickness accuracy of the part is reduced by half. Thus, with the conventional method of forming individual lens elements, it is difficult to reduce the lens thickness along the optical axis AX after bonding, to achieve higher accuracy, and to improve the reliability of bonding.

In the present embodiment, the first substrate SP and the second substrate LP each having a large outer diameter are provided in advance. Then, the substrates are integrated by activated bonding. Subsequently, the activated and bonded substrates are made into thin pieces, each of which is processed into the plano-concave negative lens L1.

In the present embodiment, the plano-concave negative lens L1 is manufactured by the steps described above. Two substrates are activated and bonded in advance to make a composite material with a high strength (broke resistant) before processing. It is therefore possible to perform processing with high accuracy while further reducing the thickness along the optical axis AX after bonding. In addition, the bonding of two substrates is stable because the substrate surfaces that are continuous and uniform are bonded without being affected by the edges.

As a result, in the present embodiment, it is possible to activate and bond the sapphire glass so thin that it cannot be assembled into a frame, in the size of a single plano-concave negative lens L1. Subsequently, the activated and bonded substrates are processed thinly. Therefore, it is possible to form the plano-concave negative lens L1 so thin that cannot be processed as a single lens.

Figure 8:
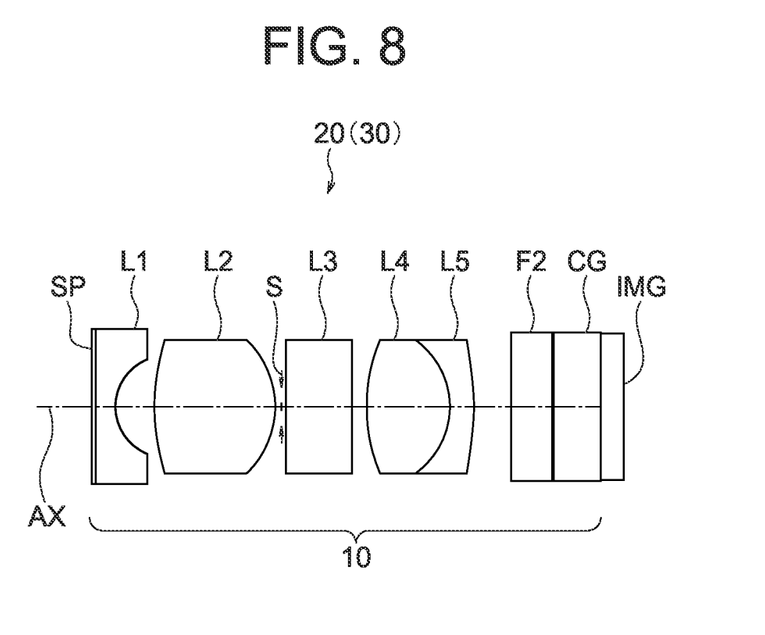
FIG. 8 is a cross-sectional view of an image pickup apparatus according to a third embodiment and an endoscope according to a fourth embodiment.

FIG. 8 is a cross-sectional view of an image pickup apparatus according to a third embodiment and an endoscope according to a fourth embodiment.

Third Embodiment

FIG. 8 is a diagram illustrating an image pickup apparatus 20 according to the third embodiment. The image pickup apparatus 20 includes an objective optical system OBL and an imager IMG. The objective optical system OBL is the objective optical system 10 described above.

The image pickup apparatus 20 of the present embodiment includes the objective optical system 10 described above. Therefore, the image pickup apparatus 20 of the present embodiment has a wide angle of view and a small outer diameter and has a lens surface at the distal end reinforced against scratches and cracks.

Fourth Embodiment

FIG. 8 is a diagram also illustrating an endoscope 30 according to the fourth embodiment. The endoscope 30 includes an objective optical system OBL and an imager IMG. The objective optical system OBL is the objective optical system 10 described above.

The endoscope 30 of the present embodiment includes the objective optical system 10 described above. Therefore, the endoscope 30 of the present embodiment has a wide angle of view and a small outer diameter and has a lens surface at the distal end reinforced against scratches and chips.

Example 1

Figure 4A:
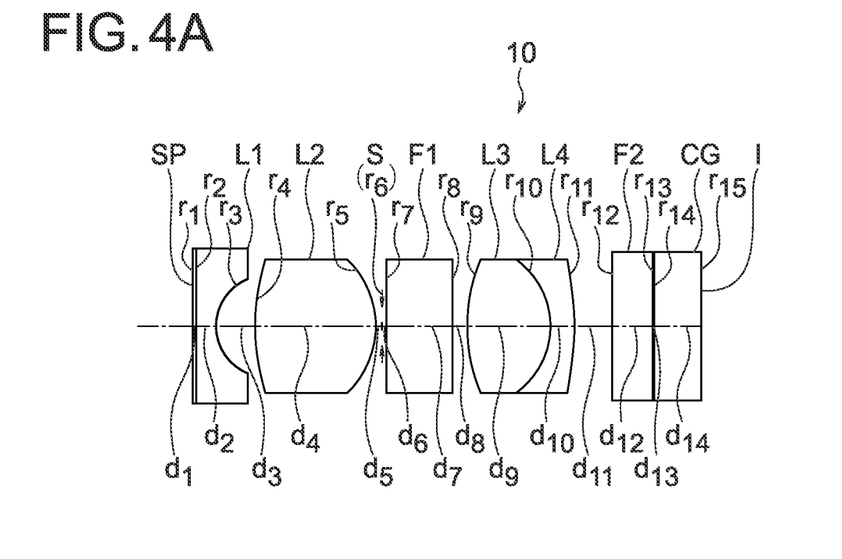
FIG. 4A is a lens cross-sectional view of the objective optical system of Example 1.

FIG. 4A is a lens cross-sectional view of an objective optical system 10 of Example 1.

The objective optical system in this example includes, in order from an object side to an image side, a flat plate SP (sapphire glass), a plano-concave negative lens L1 having a flat surface facing the object side, a biconvex positive lens L2, an aperture stop S, a parallel flat plate F1, a biconvex positive lens L3, a negative meniscus lens L4 having a convex surface facing the image side, a parallel flat plate F2, and a cover glass CG. The parallel flat plate F1 is an infrared cut-off filter. I is an image pickup surface.

The flat plate SP and the plano-concave negative lens L1 are activated and bonded. The biconvex positive lens L3 and the negative meniscus lens L4 are cemented. The parallel flat plate F2 and the cover glass CG are bonded.

Figure 4B:
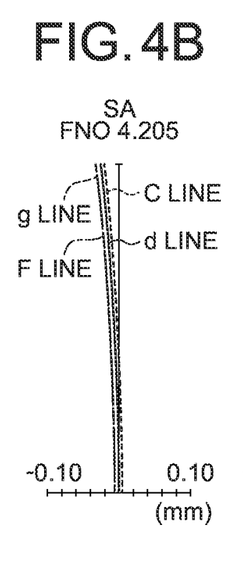
FIG. 4B, FIG. 4C, FIG. 4D, and FIG. 4E are aberration diagrams.
Figure 4C:
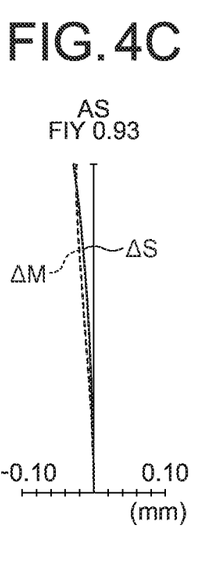
Figure 4D:
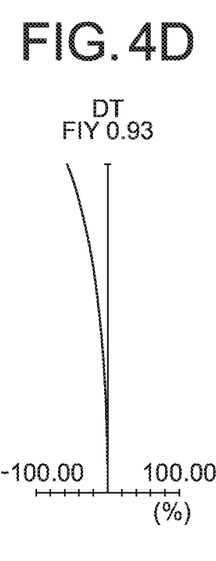
Figure 4E:
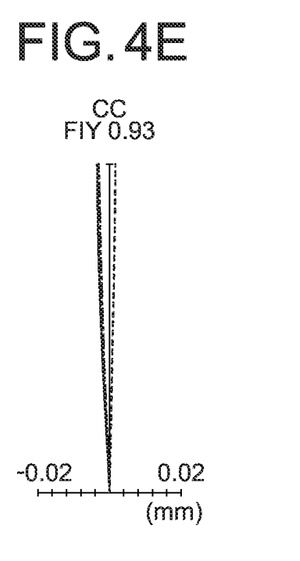

FIGS. 4B to 4E illustrate the present example, in which FIG. 4B illustrates spherical aberration (SA), FIG. 4C illustrates astigmatism (AS), FIG. 4D illustrates distortion (DT), and FIG. 4E illustrates chromatic aberration of magnification (CC). In each aberration diagram, FIY is the image height.

Example 2

Figure 5A:
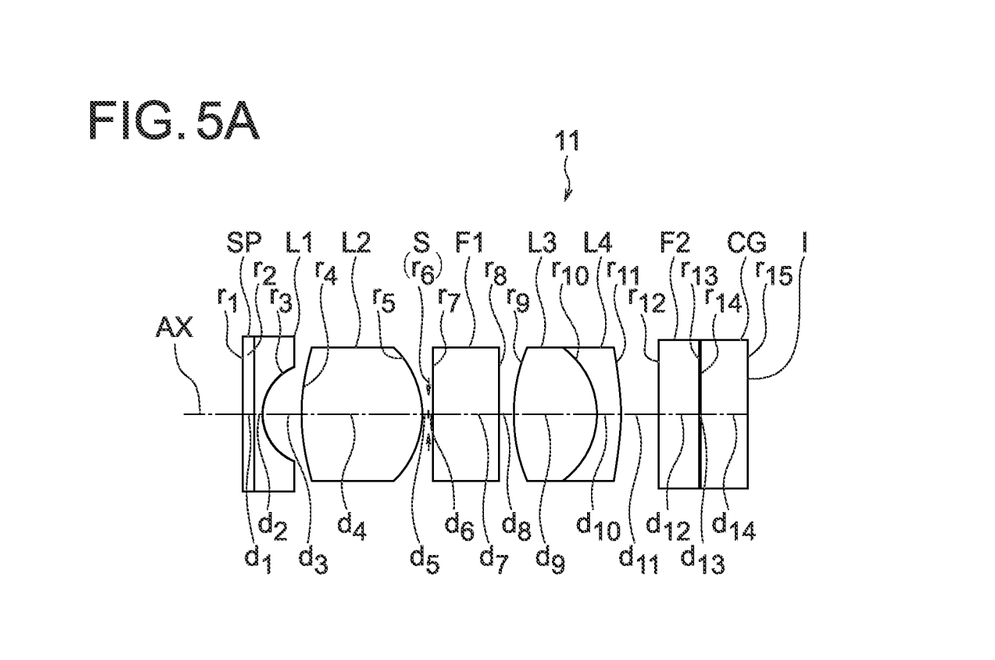
FIG. 5A is a lens cross-sectional view of the objective optical system of Example 2.

FIG. 5A is a lens cross-sectional view of an objective optical system 11 of Example 2.

The objective optical system in this example includes, in order from an object side to an image side, a flat plate SP (sapphire glass), a plano-concave negative lens L1 having a flat surface facing the object side, a biconvex positive lens L2, an aperture stop S, a parallel flat plate F1, a biconvex positive lens L3, a negative meniscus lens L4 having a convex surface facing the image side, a parallel flat plate F2, and a cover glass CG. The parallel flat plate F1 is an infrared cut-off filter. I is an image pickup surface.

The flat plate SP and the plano-concave negative lens L1 are activated and bonded. The biconvex positive lens L3 and the negative meniscus lens L4 are bonded. The parallel flat plate F2 and the cover glass CG are cemented.

Figure 5B:
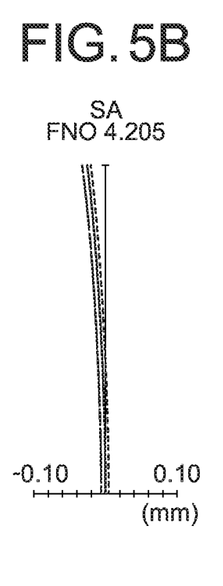
FIG. 5B, FIG. 5C, FIG. 5D, and FIG. 5E are aberration diagrams.
Figure 5C:
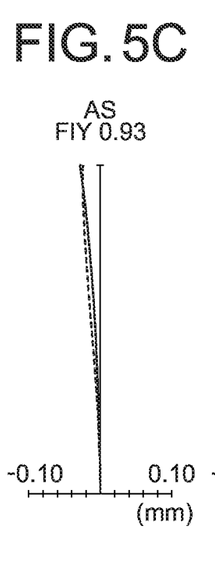
Figure 5D:
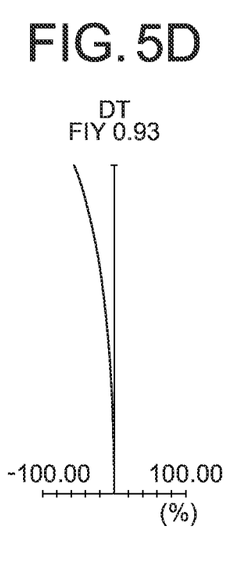
Figure 5E:
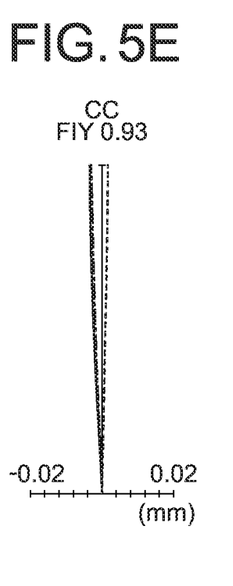

FIGS. 5B to 5E illustrate the present example, in which FIG. 5B illustrates spherical aberration (SA), FIG. 5C illustrates astigmatism (AS), FIG. 5D illustrates distortion (DT), and FIG. 5E illustrates chromatic aberration of magnification (CC).

Example 3

Figure 6A:
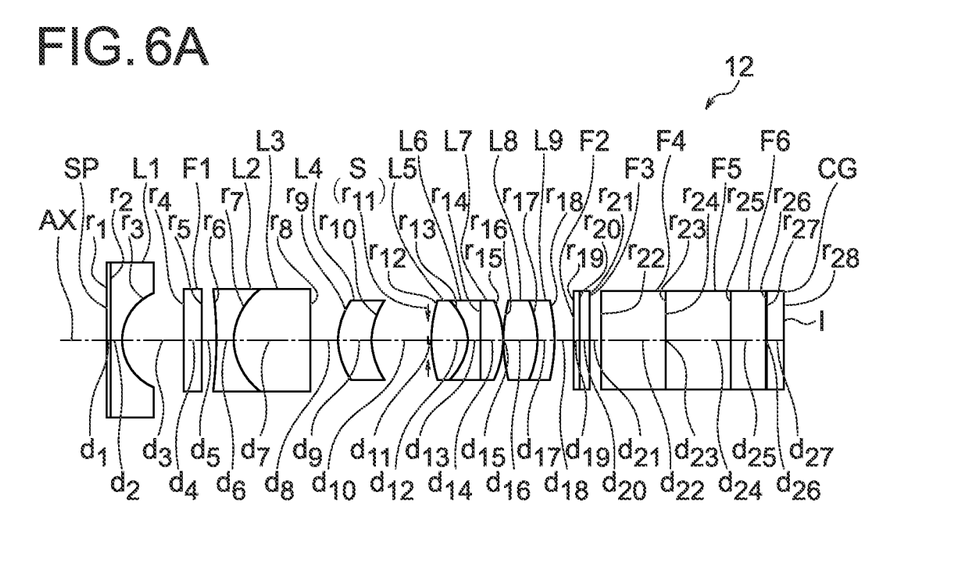
FIG. 6A is a lens cross-sectional view of the objective optical system of Example 3.

FIG. 6A is a lens cross-sectional view of an objective optical system 12 of Example 3.

The objective optical system in this example includes, in order from an object side to an image side, a flat plate SP (sapphire glass), a plano-concave negative lens L1 having a flat surface facing the object side, a parallel flat plate F1, a biconcave negative lens L2, a plano-convex positive lens L3 having a flat surface facing the image side, a positive meniscus lens L4 having a convex surface facing the object side, an aperture stop S, a biconvex positive lens L5, a plano-concave negative lens L6 having a flat surface facing the image side, a plano-convex positive lens L7 having a flat surface facing the object side, a biconvex positive lens L8, a negative meniscus lens L9 having a convex surface facing the image side, parallel flat plates F2, F3, F4, F5, and F6, and a cover glass CG. The parallel flat plate F1 is an infrared cut-off filter. I is an image pickup surface.

The flat plate SP and the plano-concave negative lens L1 are activated and bonded. The biconcave negative lens L2 and the plano-convex positive lens L3 are bonded. The biconvex positive lens L5, the plano-concave negative lens L6, and the plano-convex positive lens L7 are cemented. The biconvex positive lens L8 and the negative meniscus lens L9 are cemented. The parallel flat plates F2 and F3 are bonded. The parallel flat plates F4, F5, and F6 and the cover glass CG are bonded.

Figure 6B:
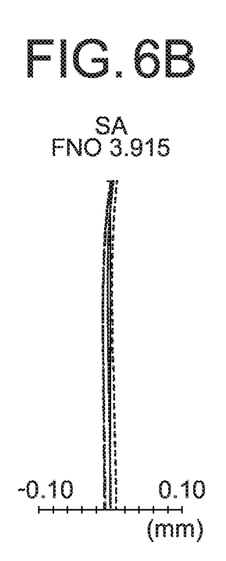
FIG. 6B, FIG. 6C, FIG. 6D, and FIG. 6E are aberration diagrams.
Figure 6C:
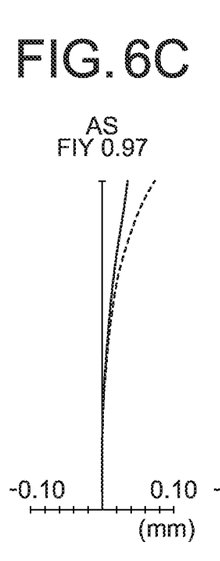
Figure 6D:
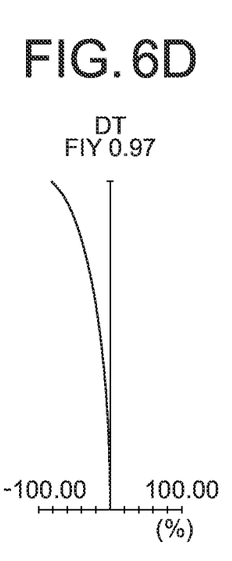
Figure 6E:
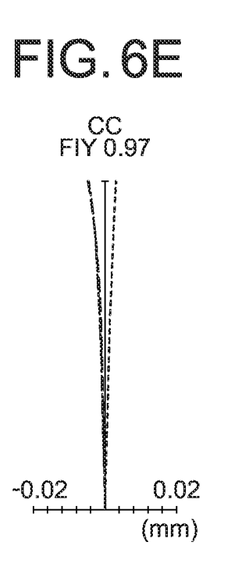

FIGS. 6A to 6E illustrate the present example, in which FIG. 6B illustrates spherical aberration (SA), FIG. 6C illustrates astigmatism (AS), FIG. 6D illustrates distortion (DT), and FIG. 6E illustrates chromatic aberration of magnification (CC).

Example 4

Figure 7A:
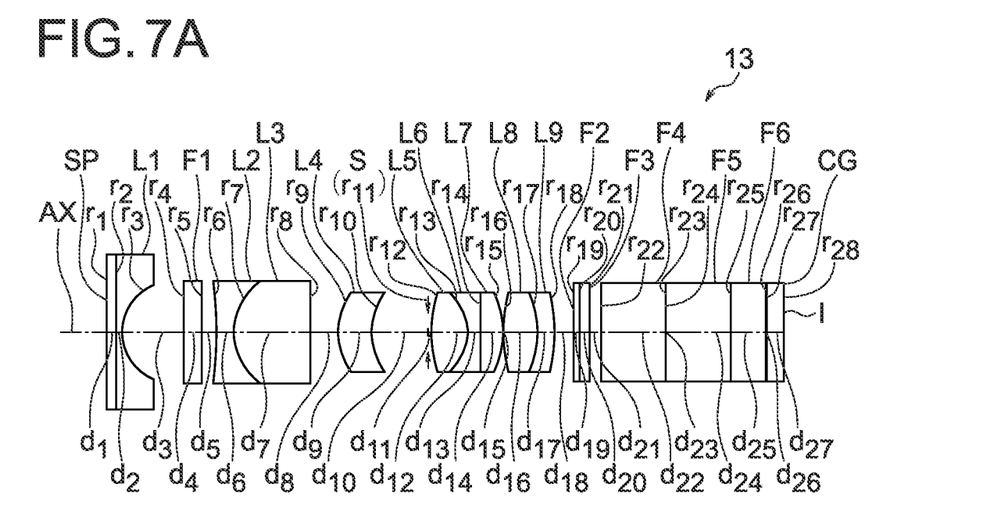
FIG. 7A is a lens cross-sectional view of the objective optical system of Example 4.

FIG. 7A is a lens cross-sectional view of an objective optical system 13 of Example 4.

The objective optical system in this example includes, in order from an object side to an image side, a flat plate SP (sapphire glass), a plano-concave negative lens L1 having a flat surface facing the object side, a parallel flat plate F1, a biconcave negative lens L2, a plano-convex positive lens L3 having a flat surface facing the image side, a positive meniscus lens L4 having a convex surface facing the object side, an aperture stop S, a biconvex positive lens L5, a plano-concave negative lens L6 having a flat surface facing the image side, a plano-convex positive lens L7 having a flat surface facing the object side, a biconvex positive lens L8, a negative meniscus lens L9 having a convex surface facing the image side, parallel flat plates F2, F3, F4, F5, and F6, and a cover glass CG. The parallel flat plate F1 is an infrared cut-off filter. I is an image pickup surface.

The flat plate SP and the plano-concave negative lens L1 are activated and bonded. The biconcave negative lens L2 and the plano-convex positive lens L3 are bonded. The biconvex positive lens L5, the plano-concave negative lens L6, and the plano-convex positive lens L7 are cemented. The biconvex positive lens L8 and the biconvex positive lens L9 are cemented. The parallel flat plates F2 and F3 are cemented. The parallel flat plates F4, F5, and F6 and the cover glass CG are cemented.

Figure 7B:
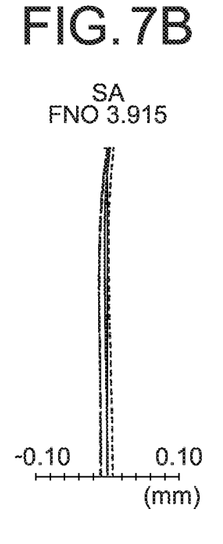
FIG. 7B, FIG. 7C, FIG. 7D, and FIG. 7E are aberration diagrams.
Figure 7C:
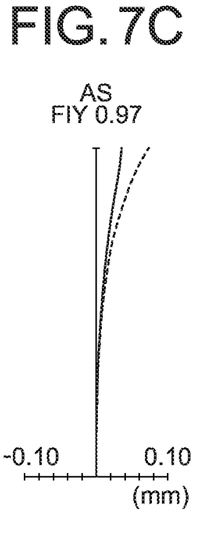
Figure 7D:
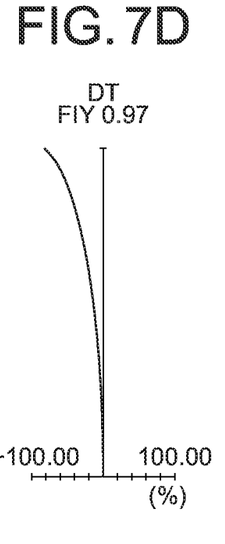
Figure 7E:
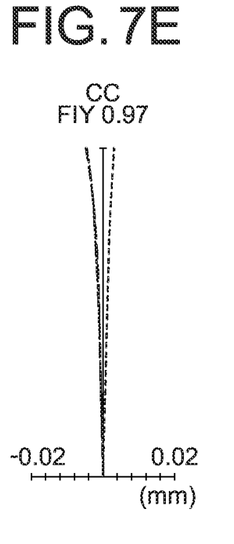

FIGS. 7A to 7E illustrate the present example, in which FIG. 7B illustrates spherical aberration (SA), FIG. 7C illustrates astigmatism (AS), FIG. 7D illustrates distortion (DT), and FIG. 7E illustrates chromatic aberration of magnification (CC).

Numerical data of the examples above is listed below. In the surface data, r is the radius of curvature of each lens surface, d is the distance between lens surfaces, and aperture is the aperture stop. nd is the refractive index of each lens for d-line, and vd is the Abbe number of each lens.

Furthermore, among the distances d between lens surfaces, d1 corresponds to t1. Among the distances d between lens surfaces, d2 corresponds to t2. In addition, the distance, the length, and the thickness in the data are indicated in units of mm.

Furthermore, in the data, the following numerical values are also listed in addition to the parameters described in the foregoing embodiments.

| FL | the focal length of the entire objective optical system |
|---|---|
| Fno | F number |
| IH | image height |
| ω | the angle of view |

Example 1

| Unit mm | | | | |
|---|---|---|---|---|
| Surface data | | | | |
| Surface no. | r | d | nd | vd |
| Object plane | ∞ | 18.8213 | 1. | |
| 1 | ∞ | 0.0359 | 1.76820 | 71.79 |
| 2 | ∞ | 0.3227 | 1.88300 | 40.76 |
| 3 | 0.8281 | 0.6005 | 1. | |
| 4 | 3.8216 | 1.8642 | 1.67003 | 47.23 |
| 5 | −1.5344 | 0.0896 | 1. | |
| 6(Stop) | ∞ | 0.0538 | 1. | |
| 7 | ∞ | 1.0755 | 1.52100 | 65.13 |
| 8 | ∞ | 0.2151 | 1. | |
| 9 | 2.8071 | 1.2727 | 1.72916 | 54.68 |
| 10 | −1.3265 | 0.4123 | 1.92286 | 18.90 |
| 11 | −3.7374 | 0.5859 | 1. | |
| 12 | ∞ | 0.5915 | 1.51633 | 64.14 |
| 13 | ∞ | 0.0179 | 1.51300 | 64.00 |
| 14 | ∞ | 0.7170 | 1.61062 | 50.49 |
| 15 | ∞ | 0. | 1. | |
| Image pickup surface | ∞ | 0. | | |

| Various data | | Unit |
|---|---|---|
| FL | 1 | mm |
| ω | 128.4506 | ° |
| Fno | 4.2523 | |
| IH | 0.9285 | mm |
| n2 | 1.883 | |
| t1 | 0.0359 | mm |
| t2 | 0.3227 | mm |
| φ1 | 2.5095 | mm |
| v1 | 7 | ppm/° C. |
| v2 | 6.4 | ppm/° C. |
| e1 | 470 | GPa |
| e2 | 127 | GPa |

Example 2

| Unit mm | | | | |
|---|---|---|---|---|
| Surface data | | | | |
| Surface no. | r | d | nd | vd |
| Object plane | ∞ | 18.8213 | 1. | |
| 1 | ∞ | 0.2061 | 1.76820 | 71.79 |
| 2 | ∞ | 0.1524 | 1.88300 | 40.76 |
| 3 | 0.8281 | 0.6005 | 1. | |
| 4 | 3.8216 | 1.8642 | 1.67003 | 47.23 |
| 5 | −1.5344 | 0.0896 | 1. | |
| 6(Stop) | ∞ | 0.0538 | 1. | |
| 7 | ∞ | 1.0755 | 1.52100 | 65.13 |
| 8 | ∞ | 0.2151 | 1. | |
| 9 | 2.8071 | 1.2727 | 1.72916 | 54.68 |
| 10 | −1.3265 | 0.4123 | 1.92286 | 18.90 |
| 11 | −3.7374 | 0.5859 | 1. | |
| 12 | ∞ | 0.5915 | 1.51633 | 64.14 |
| 13 | ∞ | 0.0179 | 1.51300 | 64.00 |
| 14 | ∞ | 0.7170 | 1.61062 | 50.49 |
| 15 | ∞ | 0. | 1. | |
| Image pickup surface | ∞ | 0. | | |

| Various data | | Unit |
|---|---|---|
| FL | 1 | mm |
| ω | 128.4514 | ° |
| Fno | 4.2523 | |
| IH | 0.9285 | mm |
| n2 | 1.883 | |
| t1 | 0.2061 | mm |
| t2 | 0.1524 | mm |
| φ1 | 2.5095 | mm |
| v1 | 7 | ppm/° C. |
| v2 | 6.4 | ppm/° C. |
| e1 | 470 | GPa |
| e2 | 127 | GPa |

Example 3

| Unit mm | | | | |
|---|---|---|---|---|
| Surface data | | | | |
| Surface no. | r | d | nd | vd |
| Object plane | ∞ | 22.0695 | 1. | |
| 1 | ∞ | 0.0736 | 1.76820 | 71.79 |
| 2 | ∞ | 0.4414 | 1.88300 | 40.76 |
| 3 | 1.7920 | 1.8538 | 1. | |
| 4 | ∞ | 0.5885 | 1.49400 | 75.01 |
| 5 | ∞ | 0.4414 | 1. | |
| 6 | −10.8567 | 0.5150 | 1.88300 | 40.76 |
| 7 | 2.0319 | 2.3541 | 1.84666 | 23.78 |
| 8 | ∞ | 0.9269 | 1. | |
| 9 | 2.1246 | 1.0299 | 1.48749 | 70.23 |
| 10 | 2.1849 | 1.7508 | 1. | |
| 11(Stop) | ∞ | 0.0883 | 1. | |
| 12 | 3.8563 | 1.1182 | 1.63854 | 55.38 |
| 13 | −1.6508 | 0.4414 | 1.88300 | 40.76 |
| 14 | ∞ | 0.7209 | 1.69895 | 30.13 |
| 15 | −3.4414 | 0.0441 | 1. | |
| 16 | 6.8607 | 1.0593 | 1.48749 | 70.23 |
| 17 | −3.5885 | 0.5002 | 1.95906 | 17.47 |
| 18 | −6.4384 | 0.5468 | 1. | |
| 19 | ∞ | 0.1471 | 2.20890 | 21.93 |
| 20 | ∞ | 0.2943 | 1.51633 | 64.14 |
| 21 | ∞ | 0.3604 | 1. | |
| 22 | ∞ | 2.0789 | 1.63854 | 55.38 |
| 23 | ∞ | 0.0207 | 1.51975 | 64.00 |
| 24 | ∞ | 1.9378 | 1.63854 | 55.38 |
| 25 | ∞ | 1.1742 | 1.63854 | 55.38 |
| 26 | ∞ | 0.0177 | 1.51975 | 64.00 |
| 27 | ∞ | 0.5150 | 1.50510 | 63.26 |
| 28 | ∞ | 0. | 1. | |
| Image pickup surface | ∞ | 0. | | |

| Various data | | Unit |
|---|---|---|
| FL | 1 | mm |
| ω | 159 | ° |
| Fno | 3.9344 | |
| IH | 0.9681 | mm |
| n2 | 1.883 | |
| t1 | 0.0736 | mm |
| t2 | 0.4414 | mm |
| φ1 | 5.0024 | mm |
| v1 | 7 | ppm/° C. |
| v2 | 6.4 | ppm/° C. |
| e1 | 470 | GPa |
| e2 | 127 | GPa |

Example 4

| Unit mm | | | | |
|---|---|---|---|---|
| Surface data | | | | |
| Surface no. | r | d | nd | vd |
| Object plane | ∞ | 22.0695 | 1. | |
| 1 | ∞ | 0.2943 | 1.76820 | 71.79 |
| 2 | ∞ | 0.2207 | 1.88300 | 40.76 |
| 3 | 1.7920 | 1.8538 | 1. | |
| 4 | ∞ | 0.5885 | 1.49400 | 75.01 |
| 5 | ∞ | 0.4414 | 1. | |
| 6 | −10.8567 | 0.5150 | 1.88300 | 40.76 |
| 7 | 2.0319 | 2.3541 | 1.84666 | 23.78 |
| 8 | ∞ | 0.9269 | 1. | |
| 9 | 2.1246 | 1.0299 | 1.48749 | 70.23 |
| 10 | 2.1849 | 1.7508 | 1. | |
| 11(Stop) | ∞ | 0.0883 | 1. | |
| 12 | 3.8563 | 1.1182 | 1.63854 | 55.38 |
| 13 | −1.6508 | 0.4414 | 1.88300 | 40.76 |
| 14 | ∞ | 0.7209 | 1.69895 | 30.13 |
| 15 | −3.4414 | 0.0441 | 1. | |
| 16 | 6.8607 | 1.0593 | 1.48749 | 70.23 |
| 17 | −3.5885 | 0.5002 | 1.95906 | 17.47 |
| 18 | −6.4384 | 0.5468 | 1. | |
| 19 | ∞ | 0.1471 | 2.20890 | 21.93 |
| 20 | ∞ | 0.2943 | 1.51633 | 64.14 |
| 21 | ∞ | 0.3604 | 1. | |
| 22 | ∞ | 2.0789 | 1.63854 | 55.38 |
| 23 | ∞ | 0.0207 | 1.51975 | 64.00 |
| 24 | ∞ | 1.9378 | 1.63854 | 55.38 |
| 25 | ∞ | 1.1742 | 1.63854 | 55.38 |
| 26 | ∞ | 0.0177 | 1.51975 | 64.00 |
| 27 | ∞ | 0.5150 | 1.50510 | 63.26 |
| 28 | ∞ | 0. | 1. | |
| Image pickup surface | ∞ | 0. | | |

| Various data | | Unit |
|---|---|---|
| FL | 1 | mm |
| ω | 159 | ° |
| Fno | 3.9344 | |
| IH | 0.9681 | mm |
| n2 | 1.883 | |
| t1 | 0.2943 | mm |
| t2 | 0.2207 | mm |
| φ1 | 5.0024 | mm |
| v1 | 7 | ppm/° C. |
| v2 | 6.4 | ppm/° C. |
| e1 | 470 | GPa |
| e2 | 127 | GPa |

Values of the conditional expression in each examples are shown below.

| Conditional expression | Example1 | Example2 |
|---|---|---|
| (1) φ1/t1 | 70 | 12.173 |
| (2) t1/t2 | 0.111 | 1.352 |
| (3) (t1/t2) × (e1/e2) | 0.411 | 5 |
| (4) \|v1 − v2\|/Max(v1, v2) | 0.085 | 0.085 |
| (5) ω | 128.45 | 128.45 |
| (6) n2 | 1.883 | 1.883 |
| (7) φ1/(t1 + t2) | 7.00 | 7.00 |

| Conditional expression | Example3 | Example4 |
|---|---|---|
| (1) φ1/t1 | 68 | 17 |
| (2) t1/t2 | 0.166 | 1.333 |
| (3) (t1/t2) × (e1/e2) | 0.617 | 4.934 |
| (4) \|v1 − v2\|/Max(v1, v2) | 0.085 | 0.085 |
| (5) ω | 159 | 159 |
| (6) n2 | 1.883 | 1.883 |
| (7) φ1/(t1 + t2) | 9.71 | 9.71 |

The objective optical system described above may simultaneously satisfy a plurality of configurations. Doing so is preferable to obtain a favorable objective optical system. Furthermore, preferable configurations may be combined as desired. Furthermore, in each conditional expression, only the upper limit value or the lower limit value in the numerical range of a more limited conditional expression may be defined.

Although various embodiments of the present disclosure have been described above, the present disclosure is not intended to be limited by those embodiments, and embodiments that are constructed by appropriately combining the configurations of these embodiments without departing from the spirit fall within the scope of the present disclosure.

The bonding between the flat plate SP and the plano-concave negative lens L1 is not limited to the activated bonding described above.

Furthermore, according to a preferred mode of the present embodiment, the flat plate SP is preferably a transparent material with a Vickers hardness of 14 GPa or higher. In addition, the flat plate SP is preferably sapphire glass or transparent ceramics.

The flat plate SP is not limited to sapphire and may be any material harder than the plano-concave negative lens L1. For example, the flat plate SP may be glass with a Vickers hardness of 14 GPa or higher, monocrystal or polycrystal such as YAG or YSZ, or transparent ceramics with a Vickers hardness of 14 GPa or higher such as alumina or $Si_3N_4$.

Examples of the Vickers hardness of the materials used for the flat plate SP are listed below.

| Material | Vickers hardness [GPa] |
| --- | --- |
| Sapphire | 22.5 |
| Polycrystalline YAG | 15 |
| Monocrystalline YSZ | 19.5 |
| Alumina | 15.2 |
| $Si_3N_4$ | 14 |

According to the present disclosure, it is possible to provide an objective optical system, an image pickup apparatus, an endoscope that have a wide angle of view and a small outer diameter and have a lens surface at the distal end reinforced against scratches and cracks, as well as a method of manufacturing an objective optical system.

As described above, the present disclosure is suitable for an objective optical system, an image pickup apparatus, an endoscope that have a wide angle of view and a small outer diameter and have a lens surface at the distal end reinforced against scratches and cracks, as well as a method of manufacturing an objective optical system.

What is claimed is:

1. An objective optical system comprising:
   a flat plate disposed closest to an object side; and
   a plano-concave negative lens having a flat surface facing the object side,
   wherein:
   the flat plate is made of a transparent material harder than a material of which the plano-concave lens is made,
   the flat plate and the plano-concave lens have equal diameters and are bonded, and
   the following Conditional Expressions (1), (3), and (7) are satisfied:

$$10 \leq \varphi1/t1 \leq 70 \quad (1)$$

$$0.4 \leq (t1/t2) \times (e1/e2) \leq 5 \quad (3)$$

$$7 \leq \varphi1/(t1+t2) \leq 9.71 \quad (7)$$

where:
φ1 is an outer diameter of the flat plate,
t1 is a thickness of the flat plate,
t2 is a thickness of the plano-concave negative lens along an optical axis,
e1 is an elastic modulus of the flat plate, and
e2 is an elastic modulus of the plano-concave negative lens.

2. The objective optical system according to claim 1, wherein the flat plate and the plano-concave negative lens are bonded by activated bonding.

3. The objective optical system according to claim 1, wherein the following Conditional Expression (2) is satisfied:

$$0.1 \leq t1/t2 \leq 1.4 \quad (2).$$

4. The objective optical system according to claim 1, wherein the following Conditional Expression (4) is satisfied:

$$|v1-v2|/\text{Max}(v1,v2) \leq 0.2 \quad (4)$$

where:
v1 is a coefficient of linear expansion of the flat plate,
v2 is a coefficient of linear expansion of the plano-concave negative lens, and
Max(v1,v2) is a larger value of v1 and v2.

5. The objective optical system according to claim 1, wherein the following Conditional Expression (5) is satisfied:

$$120° \leq \omega \quad (5)$$

where ω is an angle of view of the objective optical system.

6. The objective optical system according to claim 1, wherein the following Conditional Expression (6) is satisfied:

$$1.8 \leq n2 \leq 2.2 \quad (6)$$

where n2 is a refractive index of the plano-concave negative lens for d-line.

7. The objective optical system according to claim 1, wherein the following Conditional Expression (1') is satisfied:

$$12 \leq \varphi1/t1 \leq 50 \quad (1').$$

8. The objective optical system according to claim 1, wherein the following Conditional Expression (1'') is satisfied:

$$14 \leq \varphi1/t1 \leq 34 \quad (1'').$$

9. The objective optical system according to claim 1, wherein the following Conditional Expression (2') is satisfied:

$$0.2 \leq t1/t2 \leq 1.2 \quad (2').$$

10. The objective optical system according to claim 1, wherein the following Conditional Expression (2'') is satisfied:

$$0.4 \leq t1/t2 \leq 1.0 \quad (2'').$$

11. The objective optical system according to claim 1, wherein the flat plate is made of a transparent material with a Vickers hardness of 14 GPa or higher.

12. The objective optical system according to claim 1, wherein the flat plate is made of sapphire glass or transparent ceramics.

13. An image pickup apparatus comprising:
   an objective optical system; and
   an imager,
   wherein the objective optical system is the objective optical system according to claim 1.

14. An endoscope comprising:
   an objective optical system; and
   an imager,
   wherein the objective optical system is the objective optical system according to claim 1.

15. A method of manufacturing an objective optical system, the method comprising:

providing a first substrate made of a transparent material;

providing a second substrate made of an optical glass to form a plano-concave negative lens;

activating and bonding the first substrate and the second substrate;

making the activated and bonded first substrate and second substrate into thin pieces, the first substrate and the second substrate each having dimensions corresponding to a plurality of the plano-concave negative lenses; and performing lens processing on the second substrate after the step of making the thin pieces, wherein:

the first substrate is made of a material harder than a material of which the second substrate is made, the first substrate is made of sapphire glass, a plane perpendicular to a C-axis of monocrystalline sapphire glass in the first substrate is activated and bonded to the second substrate, and the following Conditional Expressions (1) and (7) are satisfied:

$$10 \leq \varphi 1/t1 \leq 70 \tag{1}$$

$$7 \leq \varphi 1/(t1+t2) \leq 9.71 \tag{7}$$

where:

$\varphi 1$ is an outer diameter of the first substrate, t1 is a thickness of the first substrate, and t2 is a thickness of the second substrate along an optical axis.

16. The method according to claim 15, wherein the step of activating and bonding includes a surface activated bonding step or a plasma activated bonding step.

* * * * *